(12) United States Patent
Molsberger

(10) Patent No.: US 10,857,355 B2
(45) Date of Patent: Dec. 8, 2020

(54) THERAPEUTICALLY APPLICABLE MULTICHANNEL DIRECT CURRENT DELIVERY DEVICE

(71) Applicant: Albrecht Molsberger, Düsseldorf (DE)

(72) Inventor: Albrecht Molsberger, Düsseldorf (DE)

( * ) Notice: Subject to any disclaimer, the term of this patent is extended or adjusted under 35 U.S.C. 154(b) by 362 days.

(21) Appl. No.: 15/313,481

(22) PCT Filed: May 23, 2014

(86) PCT No.: PCT/EP2014/060742
§ 371 (c)(1),
(2) Date: Nov. 22, 2016

(87) PCT Pub. No.: WO2015/176778
PCT Pub. Date: Nov. 26, 2015

(65) Prior Publication Data
US 2017/0136235 A1   May 18, 2017

(51) Int. Cl.
*A61N 1/04* (2006.01)
*A61N 1/05* (2006.01)
*A61N 1/20* (2006.01)
*A61H 39/00* (2006.01)

(52) U.S. Cl.
CPC ............ *A61N 1/20* (2013.01); *A61H 39/002* (2013.01); *A61N 1/0492* (2013.01); *A61N 1/0502* (2013.01); *A61N 1/205* (2013.01)

(58) Field of Classification Search
CPC ...... A61N 1/20; A61N 1/0492; A61N 1/0502; A61H 39/002
USPC .......................................................... 607/46
See application file for complete search history.

(56) References Cited

U.S. PATENT DOCUMENTS

| 5,195,517 A * | 3/1993 | Chen ................. A61N 1/36014 607/3 |
| 5,449,378 A | 9/1995 | Schouenborg |
| 5,697,909 A | 12/1997 | Eggers et al. |
| 9,162,055 B2 | 10/2015 | Pianca et al. |
| 2004/0097918 A1 | 5/2004 | Schonfeld |

(Continued)

FOREIGN PATENT DOCUMENTS

| DE | 102012010262 A1 | 11/2013 |
| JP | 2013-537090 A | 9/2013 |

(Continued)

OTHER PUBLICATIONS

International Search Report dated Aug. 29, 2014 for related PCT Application No. PCT/EP2014/060742.

*Primary Examiner* — Mallika D Fairchild
*Assistant Examiner* — Minh Duc G Pham
(74) *Attorney, Agent, or Firm* — Howard IP Law Group, PC

(57) ABSTRACT

A direct current delivery device includes a direct current source or a device for connecting to a direct current source, and a first electrode and a second electrode for connecting to the direct current source, wherein the first electrode is configured as a plurality of needles and the second electrode is configured as a planar electrode, as a needle or a plurality of needles directly connected to one another in an electrically conductive manner. The direct current delivery device includes one or more devices configured to maintain the current intensity constant during the individual delivery of direct current through the needles of the first electrode.

22 Claims, 1 Drawing Sheet

(56) References Cited

U.S. PATENT DOCUMENTS

| | | |
|---|---|---|
| 2004/0111128 A1 | 6/2004 | Wang |
| 2006/0085056 A1* | 4/2006 | Schouenborg ....... A61H 39/002 |
| | | 607/148 |
| 2010/0161001 A1* | 6/2010 | DiUbaldi ........... A61N 1/36031 |
| | | 607/59 |
| 2012/0143287 A1* | 6/2012 | Shodo ................ A61N 1/36034 |
| | | 607/72 |
| 2014/0276539 A1* | 9/2014 | Allison .................... A61F 7/12 |
| | | 604/500 |
| 2015/0073406 A1 | 3/2015 | Molsberger |
| 2015/0196767 A1* | 7/2015 | Ahmed ................ A61N 1/0551 |
| | | 607/48 |

FOREIGN PATENT DOCUMENTS

| | | |
|---|---|---|
| WO | 93/23112 A1 | 11/1993 |
| WO | 02/096511 A1 | 12/2002 |
| WO | 2013/175021 A1 | 11/2013 |

\* cited by examiner

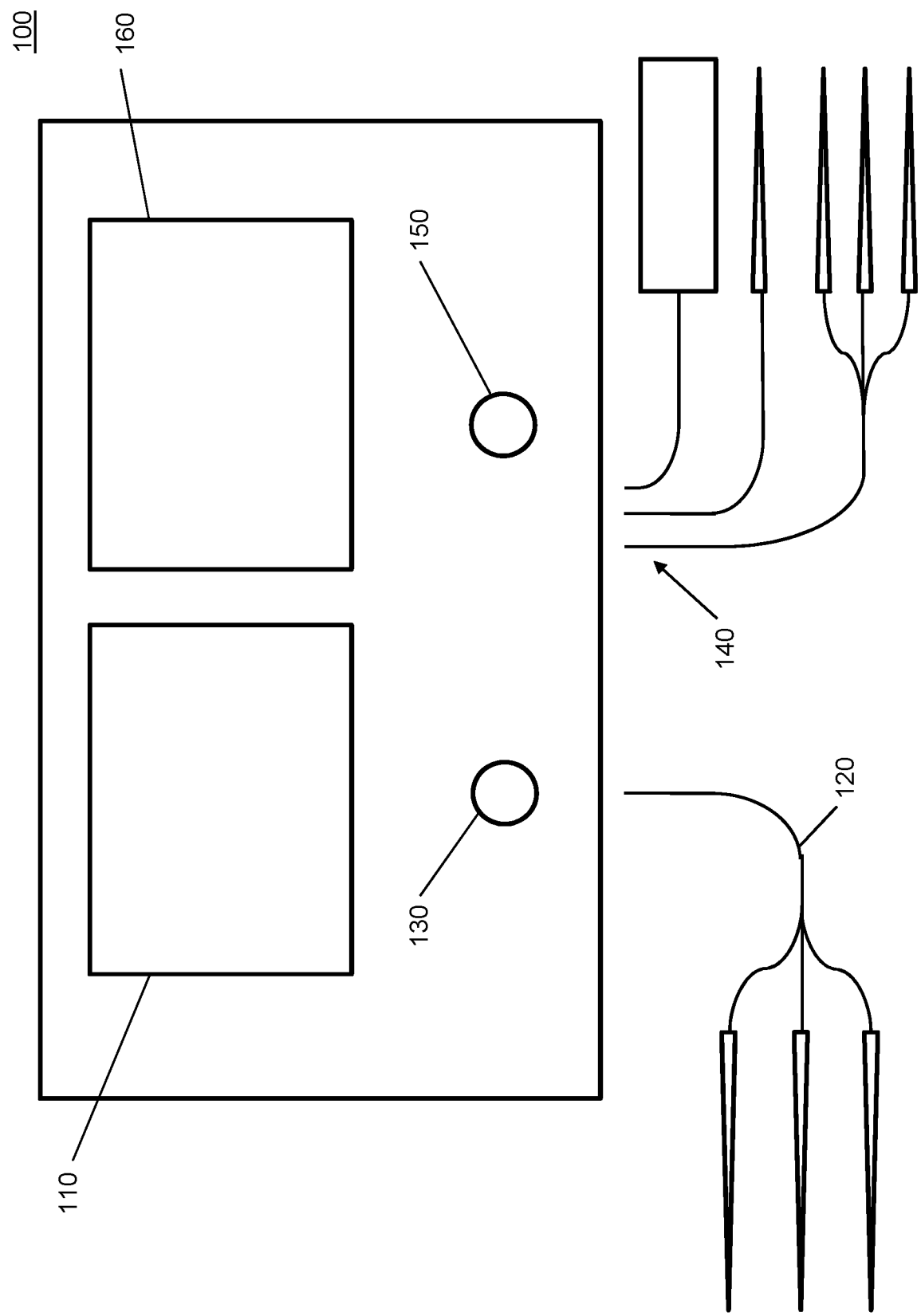

THERAPEUTICALLY APPLICABLE MULTICHANNEL DIRECT CURRENT DELIVERY DEVICE

CROSS-REFERENCE TO RELATED APPLICATIONS

This application is a national phase application under 35 U.S.C. § 371 of International Patent Application No. PCT/EP2014/060742 filed May 23, 2014, the entire contents of which are incorporated herein by reference in their entirety for all purposes.

FIELD

The present invention relates to a device for outputting direct current. The direct current output device according to the invention can be used for the therapeutic or cosmetic treatment of the human body or the body of an animal. The present invention is also additionally aimed at the direct current output device for specific application in particular procedures for the therapeutic treatment of the human body or an animal's body. The direct current output device according to the invention is particularly suitable for the treatment of inflammation and/or pain. Lastly, the invention also relates to a kit and a method for producing the direct current output device.

BACKGROUND

Many of the medical or cosmetic conditions affecting the human or animal body are local in nature. A medically relevant condition is present in the case of diseases or impairments to the functioning of the body. In these cases a therapeutic treatment is absolutely appropriate. In the case of irritations, which in the context of the present invention include relatively minor impairments or complaints of the human or animal body that do not constitute a disease or disorder and do not require treatment, then at least a cosmetic, non-therapeutic treatment is often useful.

The present invention relates to both the non-therapeutic cosmetic treatment of cosmetic impairments caused by (mainly local) irritations and to the creation of new treatment options for (mainly local) medically relevant impairments of the human or animal body.

The concept of treatment also includes prophylaxis. "Local" means that a certain area affected by the irritation or medically relevant impairment can be found on or in the body. This area is preferably locally circumscribed and more preferably, precisely identifiable. The area (e.g. the irritated area, area of inflammation, painful area) is associated with particular symptoms and triggers the impairment or complaint, or is associated therewith.

Impairments of the human body or body of an animal which arise from local inflammations and pain conditions are, for example, aseptic inflammations—often due to local stresses (distortions, cases of insertion tendinitis) or also neuropathic pains. In the orthopedic area, local inflammation and pain conditions occur in particular in connection with tissue injuries, in particular of muscles (e.g. muscle trauma), nerves, skin or skeletal support system, vascular injuries or also in connection with nerve inflammation, inflammation of the tendons or bones, or scar formation. There is often a locally defined area in which the complaints can be detected.

If an impairment meets the criterion of a disease or disturbance to the functioning of the body, it is normally indicated as requiring therapeutic treatment. Examples of a purely cosmetic impairment by contrast are wrinkles, caused for example by increased muscle tone, poor posture and pain-avoiding posture, or purely unsightly skin changes such as areas of redness.

Methods and means for therapeutic or cosmetic treatment of medical or cosmetic impairments and complaints are known. Even if in some cases e.g. physiotherapy can provide relief, as a rule however, specific pharmaceutical agents are used, primarily cortisone, non-steroidal anti-inflammatory drugs, analgesics and related substances. In addition to the desired (local) effect, these usually have unwanted local side effects (e.g. in the case of local applications of cortisone, aseptic inflammations) and/or systemic side effects, and these can have adverse effects on the metabolism and hormone balance. In many cases, the conventional therapeutic methods cannot treat a chronic form of a disease. It is therefore advisable to take into consideration alternatives to the use of (exogenous) active substances.

A number of treatment options also exist which are known to make increased use of the intrinsic healing capacities of the human or animal body. A widely used technique is acupuncture and its variants, a technique based on traditional Chinese medicine (TCM).

Acupuncture is generally recognized as being effective and of low risk in the treatment of certain complaints, such as chronic pain (e.g. headache, migraine). Thus since 1 Jan. 2007 all the German statutory health insurance funds have covered acupuncture treatments, in particular those based on the results of large-scale and randomized trials (GERAC, German acupuncture trials), in the treatment of chronic lower back pain and chronic knee pain in osteoarthritis of the knee. Private health insurance companies pay for acupuncture services for the treatment of pain, and usually for other indications as well, on a case-by-case basis. The "Cochrane reviews" of 2009 classify acupuncture as "a valuable non-pharmacological treatment option for patients with frequent episodic tension headache" and conclude that the "acupuncture treatment of migraine is at least as effective, possibly even more effective, than a drug-based prophylactic therapy, and with fewer adverse side-effects".

It was shown in the GERAC studies that no significant difference existed between acupuncture treatment at points that follow the guidelines of TCM and acupuncture treatment at other points (so-called "fake acupuncture"). Positive therapeutic or cosmetic effects have been demonstrated for both forms of acupuncture when applied to local inflammation and pain conditions. Nowadays other forms of acupuncture are also commonly used that are not derived from the traditional theoretical framework of TCM.

Endogenous physiological electrical fields are known in biology. These fields are in the range of 70 mV/mm (nerve growth in chickens), 140 mV/mm (wound healing in rats), 600 mV/mm (eye lens of vertebrates) up to 1500 mV/mm (development of the neuronal tube in the axolotl). Depending on the internal resistance of the relevant biological tissue, these give rise to currents of 10-200 µA. Endogenous electrical fields build up for a period lasting from hours to weeks, for example in the region of the wound, in the region of the active cell growth and in cell migration, and appear to be essential for the regulation of cell behavior.

The merits of the use of exogenous electric fields in the fields of medicine and cosmetics are known. The types of fields regularly used are strong and/or time-varying fields, wherein the temporal variability is effected by alternating voltage or short direct-current voltage pulses. These strong electric fields used for therapeutic purposes up to now are generated, for example, by high voltages and in many cases by strong currents. In this context, AC and AC-pulsed current devices are used, in order to counteract electrolytic effects at the electrodes used and in particular on the body tissue.

One known method is transcutaneous electrical nerve stimulation (TENS). In this technique low-frequency (1-100 Hz) biphasic alternating current pulses are used for pain relief, primarily for short-term "electrical analgesia". The voltage level is up to 70 V with a pulse width of approx. 250 µs at a current intensity of up to 90 mA. The effect is primarily based on an increase in the central release of endorphins. It is unclear whether local or longer-term effects are also obtained in the affected tissues.

Also known is the technique of electro-acupuncture. Its action mechanism targets the release of central pain-relieving substances, in particular of encephalins, endorphins and dynorphins.

As described in document US 2004/0111128 A1, electro-acupuncture also uses alternating currents. In electro-acupuncture a low-frequency stimulation current is applied (Springer Lexicon of Medicine), where the frequency of the electrical signal is either fixed or variable (2-10,000 Hz). As in the case of TENS, relatively high currents are used that can be between 2 and 15 mA. These can be applied in pulsed mode at this intensity with a pulse width of approximately 0.3-0.6 ms. In order to avoid electrolytic effects at the junction between the electrode and biological tissue when using these high currents, the polarity is alternated (alternating current/AC). Accordingly, the electrical parameters used in electro-acupuncture will in every case include frequency and intensity (see a summary of parameters for electro-acupuncture accessible under the URL http://www.icmart.org/index.php?id=198.0.0.1.0.0 originating from a conference of the International Council on Medical Acupuncture and Related Techniques).

In summary, the known devices for TENS or electro-acupuncture involve technically complex circuitry, they operate with high currents, short pulses and AC power at specific frequencies. In spite of this, the stimulation dose is often not controllable. These means and methods of the prior art are aimed at pain relief, which is based on a central analgesic effect. They are not focused on any local action (such as an anti-inflammatory or regenerative effect).

In tumor therapy a direct-current Galvano-therapy with high current intensities of 60-80 mA at a voltage of 6-35 V is known. This therapy is intended to bring about a destruction of the tumor tissue, for example by necrosis. A destruction of tissue is therefore in this case not an undesirable effect to be avoided, but on the contrary, is explicitly strived for. The method makes use of the increased conductivity of tumor tissue in comparison to healthy tissue, so as to selectively concentrate the current flow in the tumor tissue and cause the decay of the tumor due to electrolytic and necrotizing effects.

Direct current is also used for the transcutaneous transport of ionisable drugs (iontophoresis). The voltages used are about 36-60 V at currents of about 10-30 mA. In order to avoid local tissue damage and to be able to transport a high dose of active ingredients electrophoretically, large skin electrodes have to be placed on the skin.

Another known technique is the application of large-area wet cellulose electrodes to the scalp for stimulating the central nervous system (transcranial direct current stimulation tDCS), for example in the case of tinnitus. In this technique, a current of up to 1 mA and a voltage of 8-25 V are used with a constant pulsating current.

It is well known that the corresponding electrical fields generated by weak direct current promote growth of blood vessels, due inter alia to the release of VEGF and its influence on endothelial cells. They cause a movement and rearrangement of cell membrane receptors, increase the division rate of particular cells and accelerate cell migration of epithelial cells. This cell migration takes place away from the anode (positive pole) and towards the cathode (to the negative pole). In animal experiments, there are indications that the rate of peripheral nerve regeneration after spinal cord trauma can be accelerated, the axons of the nerve cells growing towards the cathode, which must be positioned cranially over about three weeks. Clinical studies in humans indicate an acceleration of wound healing due to electrical fields.

Document DE 10 2012 010 262 discloses a direct current output device which comprises a means for maintaining the current intensity constant during the delivery of the DC current. There is, however, no information in the document on which specific currents must be kept constant, and in particular no information on how individual currents are held constant in the individual needles.

The foregoing statements, together with the description of exemplary embodiments contained in the present text, do not entail the exclusion of particular embodiments or features.

SUMMARY

The technical problem addressed by the present invention is to provide new means and methods with which local impairments of the human body or the body of an animal, in particular those caused by inflammation and/or pain, can be alleviated or eliminated.

Preferably, the means and methods according to the invention allow a more effective, safer and more reproducible application and/or with fewer side effects, and/or have a faster acting and/or longer-term effect than the means and methods from the prior art. The means and methods according to the invention preferably allow the treatment of local impairments that either are not appropriately treated with the means from the prior art or cannot be treated at all.

The technical problem is solved in accordance with a first aspect of the present invention by a direct current output device, comprising a direct current source or a device for connecting to a direct current source, and a first electrode and a second electrode for connecting to the direct current source, wherein the first electrode is designed as a multiplicity of needles and the second electrode is designed as a flat electrode (preferably an adhesive electrode), as a needle or a multiplicity of electrically conductive needles directly connected to one another, characterized in that the direct current output device comprises one or more means for holding each current intensity constant during the individual output of direct current through needles of the first electrode (in particular in the event of a change in resistance connected to a needle of the first electrode), wherein the constant current preferably applies to all needles of the first electrode.

A preferred form of the direct current output device according to the invention is one in which the needles of the first electrode are not directly electrically conductively connected to each other. Also preferred is a direct current output device according to the invention in which the second electrode is designed as a flat electrode (adhesive electrode).

The term "adhesive electrode" is in this case understood to mean a flat electrode that can be applied to the (possibly depilated) skin surface and can be fixed there (possibly by using an additional material mediating or improving the conductivity, such as an electrode gel or paste), preferably by adhesion.

A "direct" electrically conductive connection is understood to mean an electrically conductive connection by means of a simple cable or other type of electrically conductive connection without intermediately connected electrical components. This would exclude, for example, an electrically conductive connection which is based solely on the fact that components of a circuit, such as resistors, are arranged between the two connected elements.

For the purposes of the present application a flat, two-dimensional electrode is sometimes also referred to as a "pad".

According to a second aspect, the present invention also relates to the direct current output device according to the invention for use in the treatment of inflammation and/or pain conditions, especially of the muscles, nerves, tendons or bones.

In other words, the subject matter of this aspect of the present invention is also the use of the direct current output device according to the invention for treating cases of inflammation and/or pain, in particular of the muscles, nerves, tendons or bones, or the use of the direct current output device for producing a therapeutic device for treating cases of inflammation and/or pain, in particular of the muscles, nerves, tendons or bones. This aspect of the present invention also relates to a method for treating cases of inflammation and/or pain, in particular of the muscles, nerves, tendons or bones of a patient who requires such treatment, which comprises allowing the direct current output device according to the invention to be applied to the body of the patient.

The technical problem addressed by the present invention is also solved in accordance with a third aspect by means of a kit for producing a direct current output device according to the invention (preferably as described above), which comprises: a multiplicity of needles for use as a first electrode, a flat electrode (e.g. an adhesive electrode), a needle or a multiplicity of needles for use as a second electrode, one or more means for holding each current intensity constant during the individual output of direct current using needles of the first electrode connected to a direct current source (or: using the needles connected to a direct current source), (in particular in the event of a change in resistance connected to a needle of the first electrode), and optionally, means for the direct electrically conductive connection of a multiplicity of needles.

The word "comprising" also includes the meaning of "consisting of" and in preferred embodiments has the latter interpretation, except where the context demands otherwise. The same applies to the variants of the term, such as "comprise" and "consist of".

Direct current is understood as meaning an electric current whose direction does not change and whose time-averaged current intensity does not substantially change under constant external conditions. The direct current is preferably a "pure" direct current, the intensity of which does not change substantially or does not change at all, under constant external conditions. However, certain temporal fluctuations are possible, in particular a "pulsed" direct current, in which the current intensity periodically oscillates about a particular mean value, but without the current direction changing. The direct current is therefore preferably a direct current which oscillates about a previously set (preferably constant) value. The oscillation preferably occurs at a frequency between 0.001 and 10 Hz, in particular between 0.01 and 1 Hz, for example, 0.1 Hz. The oscillation waveform is preferably rectangular, saw-toothed and in particular, sinusoidal. The deviation of the direct current is preferably 50% of the previously set value (i.e. the values move between 150% and 50% of the previously set value), and in particular 40%, 30%, 20%, 15%, 10%, 7.5%, 5%, 2.5% or 1%.

The present invention is based on the discovery that weak direct current can alleviate the above-mentioned medical or cosmetic impairments and complaints when it acts on the body via an electrode in a local DC voltage electric field. The effects occur even if the direct current is very weak. A particularly well reproducible effect can be achieved if the direct current is constant.

One of the findings underlying the present invention then, is the fact that the effect is particularly beneficial (e.g. with regard to the reproducibility of the effect, the strength of the effect, the rapidity of the onset of action, duration of continuation of the effect and/or the ability to treat particular impairments or complaints), when not only is the current intensity of the direct current maintained at a constant level overall, but when the respective current intensity is held constant during the individual supply of direct current through the needles of the first electrode. In other words, the relevant needles of the first electrode output a constant current intensity as a whole (preferably each one of the needles), and not just of the first electrode. In this way, by providing one or more means for respectively maintaining a constant current intensity of the direct current output by (the) individual needles of the first electrode, a multi-channel device is produced. Each individual channel, i.e. the current intensity of the individual needles of the first electrode, can thus be held constant. The current intensity output by an individual needle of the first electrode is designated hereafter as the "individual current intensity". The direct current output device according to the invention, in other words, is characterized by the fact that it comprises one or more means for keeping the individual current intensities constant.

Depending on the application, needle-shaped or flat electrodes achieve particularly good effects (e.g. two needle-shaped electrodes or one needle-shaped electrode in combination with a flat electrode, wherein a needle-shaped electrode comprises a multiplicity of needles and the flat electrode, if present, optionally comprises a multiplicity of flat structures). The applied electric field according to the invention is in the same order of magnitude as endogenous and physiological electrical fields.

The current intensity determines the intensity of the electric field in the tissue. A constant current intensity (in contrast to, for example, the setting of a constant voltage) is advantageous to the extent that any fluctuations in the resistance cannot cause fluctuations of the current intensity and in particular, no current peaks. Also, inter-individual differences in the resistance (in contrast to the setting of a constant voltage) do not give rise to different current intensities.

The direct current output device according to the invention (as described above) comprises one or more means for respectively keeping the current intensity constant during the individual output of the direct current through the needles of the first electrode (in particular in the event of a change in the resistance which is connected to (each) one or more of the needles of the first electrode). The direct current output device preferably comprises such a means for each of the needles of the first electrode. This/these means is/are designed to keep the current intensity constant during the output of the direct current, in particular when the resistance connected to (each) one or more of the needles of the first electrode changes. Without such a means the situation often exists whereby the electrical resistance of the body tissue (for example, the skin) varies during the treatment and so the current intensity also varies. It is a finding of the present invention that, by using the one or more means described above for keeping the current constant, impairments or complaints which otherwise are not or not adequately treatable, consequently become treatable. It has also been found that without such means for maintaining the current constant, due to individual differences in the resistance between the skin and tissue, which is usually in the range of 1-40 kΩ (typically 1-10 kΩ), different current intensities are observable in different individuals, which causes the treatment outcome to vary to a certain extent. When using the one or more means for maintaining a constant current, a constant treatment outcome is achieved regardless of the individually differing resistance between the skin and the tissue.

The direct current output device according to the invention enables an improvement in or elimination of cosmetically or medically determined bodily impairments and complaints. These are preferably cases of inflammation and/or pain, and in particular locally indicated. According to the invention, the use of exogenous pharmaceutical substances or medications can be reduced or completely avoided. The unwanted side effects of such substances thus occur to a lesser degree or not at all. When using the direct current output device the impairments and complaints are alleviated or eliminated or even prevented, permanently or at least in the long term. If the application is repeated, the effect can often be increased to include permanent freedom from the complaints.

The use of the invention-based direct current output device involves low risk, is effective and almost or completely free of side effects. The effect occurs rapidly and predictably. The output current dosage can be precisely controlled. A further advantage is that, according to the invention, regeneration of tissue damaged by chronic inflammation or degenerative processes is also made possible. The efficacy against inflammation and pain according to the invention is considerably better than that found in electro-acupuncture according to the prior art.

The direct current output device according to the invention has, in its application to the human or animal body, in particular an anti-inflammatory and analgesic effect, which is of advantage for example in the treatment of (particularly local) inflammations and pain, in particular of the muscles, nerves, tendons or bones. Examples of treatable conditions are aseptic inflammations, nerve pain (e.g. neuropathic pain), headache and orthopedic indications, such as pain in the thoracic spinal column or shoulders, back pain, or tendonitis (e.g. tennis elbow). The cases of inflammation/pain can be related, for example, to tissue injuries (e.g. muscles, nerves, skin or skeletal support system, vascular system), nerve inflammation, inflammation of the tendons or bones and scar formation.

The direct current output device according to the invention allows a treatment concept which is based on acupuncture. It can be applied separately or can be integrated into the normal context of acupuncture treatment. Such an approach may extend acupuncture treatment and thus improve the associated therapeutic or cosmetic treatment of complaints or impairments.

According to the invention, the direct current output device according to the invention can be used to treat the bodies of human or animal patients. The term "patient" is not to be understood restrictively in terms of a therapeutic treatment, but also covers a cosmetic treatment. Preferred patients are mammals such as horses, dogs, cats, or camels, and in particular human beings.

BRIEF DESCRIPTION OF THE DRAWINGS

FIG. 1 is a high-level block diagram of a therapeutic direct current application device according to some embodiments.

DETAILED DESCRIPTION

In a typical course of treatment the painful/inflamed area is first of all localized. For example, one or more of the (metal) needles is inserted there. The tip(s) of the needle(s) may be positioned at or outside of acupuncture points. As the first electrode the needles are connected to one pole of the direct current source, preferably the negative pole. The other pole is connected to the second electrode, which is preferably a surface adhesive electrode in another region of the body. Such a surface electrode ("pad") is preferably placed over large muscle groups or fat layers, so that no individual nerves are stimulated by the surface electrode. To perform the treatment a current is applied which is kept constant on each of the individual needles of the first electrode. Typically, the pain or inflammation subsides around 2 h after the treatment, but this can also occur later depending on the particular tissue. For example, a faster effect is found in the treatment of nerves than in the treatment of the periosteum. Normally an effect occurs within 24 h of the treatment.

The constant current is preferably maintained by automated means. The direct current output device according to the invention therefore preferably contains one or more automated means for holding each current intensity constant during the individual output of direct current through needles of the first electrode (in particular in the event of a change in resistance connected to a needle of the first electrode), preferably for each of the needles of the first electrode.

The electrical resistance R used in the treatment is defined primarily by the contact of the electrodes with the skin and possibly also by the immediate environment of the needle (s). The resistance changes frequently in the course of the treatment. In order nevertheless to ensure a constant current intensity I, the available options include the facility to change the contact surface area between the electrodes and bodily tissues, for example by changing the contact pressure of the second electrode, or to change an internal resistance of the direct current output device according to the invention.

Preferably however, a constant value of the current intensity I is ensured by an appropriate change in the voltage U that is applied to each of the individual needles of the first electrode.

FIG. 1 depicts a high-level block diagram of a therapeutic direct current application device 100 according to some embodiments. The device 100 includes a direct current output device 110, which may comprise a direct current source or a device for connecting to a direct current source. The device 100 also includes a first electrode 120 configured to be connected to a first pole 130 of the device, and a second electrode 140 configured to be connected to a second pole 150 of the device. The first electrode 120 is designed as a first plurality of electrically conductive needles and the second electrode 140 is designed as one of a flat electrode (preferably an adhesive electrode), a needle, or a second plurality of electrically conductive needles. The direct current output device 100 also includes a constant direct current means 160 for maintaining a direct current of a predetermined value through each of the first plurality of electrically conductive needles.

In the direct current output device according to the invention, the respective current intensity during the individual output of direct current through (the) needles of the first electrode can preferably be individually set, and in particular can be individually regulated.

Preferred means for keeping the current intensity constant in the direct current output device are automated and designed in the form of a regulator, which can be assembled, for example, from analogue components or designed as an integrated circuit. Such a regulator preferably comprises a means for measuring the actual current intensity (for example in the supply line to the first electrode), a means for defining a deviation from a predefined target current intensity, and a means for applying a correction of the voltage U in accordance with the deviation, in particular in proportion to the deviation (proportional regulator). A preferred direct current output device according to the invention has circuits that can be individually adjusted and regulated.

It can however also be preferred to provide a form of the direct current output device according to the invention which is technically extremely simple. A direct current output device according to the invention which comprises a plurality of series resistors is therefore also preferred; each needle of the first electrode is preferably electrically conductively connected to a series resistor. The series resistors are means for holding each current constant during the individual output of direct current through needles of the first electrode.

Preferred series resistors have a resistance of 10 kΩ to 100 kΩ, 15 kΩ to 80 kΩ, 20 kΩ to 60 kΩ, 25 kΩ to 40 kΩ, and in particular 30 kΩ. The resistances are preferably sufficient to render fluctuations of the skin resistance negligible in comparison thereto. Either fixed or variable series resistors can be used. Series resistors can be combined with one or more additional means described herein for maintaining each current intensity constant during the individual output of direct current through (the) needles of the first electrode, but they can also be used in the absence of such additional means. Series resistors can alternatively be combined with a means for maintaining the total current intensity constant during the output of the direct current, or can also be used in the absence of such a means.

According to the invention preferred direct current sources are, for example, batteries. In the context of the present invention the term "battery", in addition to batteries with a voltage of preferably 1.2 V (such as nickel metal hydride batteries) to 1.5 V (such as alkaline-manganese or zinc-carbon batteries), either alone or connected in series in sets of preferably two, three or four, also comprises accumulators and galvanic cells. A preferred battery has a voltage of 1.2 to 1.5 V and is used either alone or preferably connected in series in sets of preferably two, three or four.

Further preferred direct current sources according to the invention are mains power supplies or constant current sources. A particularly preferred direct current source is contained, for example, in the unit distributed by neuroConn GmbH (Ilmenau, Germany) under the name "DC-Stimulator". This device is used in the prior art for transcranial direct current stimulation (tDCS) of the brain. It comprises an automated means for maintaining a constant current intensity and is offered in a kit with two sponge electrodes for placing on the head for transcranial direct current stimulation, but not for electro-acupuncture. The current source included is different to the power sources used for electro-acupuncture in the prior art, because it supplies DC power instead of AC power and the output current intensity is also substantially lower. The preferred device "DC-Stimulator MC".

The direct current output device according to the invention preferably comprises a variable internal resistance for adjusting the output current intensity.

In accordance with the invention a needle is understood as meaning an elongated (preferably cylindrical) body whose length in relation to its diameter is large. A needle preferably has a pointed, in particular a conically pointed, end. The needle or needles for use as a first electrode is/are preferably designed so that their application does not cause injury to the human or animal's body. The diameter of a region to be punctured (without including a pointed end) is preferably between 0.1 and 0.8 mm, preferably between 0.2 and 0.4 mm and in particular approximately 0.3 mm, wherein an area to be punctured preferably also has a pointed end; the length of an area to be pierced is preferably between 10 and 100 mm, preferably between 20 and 50 mm and in particular approximately 30 mm. The diameter in a gripping region can be, for example, approximately 1-3 mm, in order to facilitate a simple connection of multiple needles. Preferred needles have the shape of known acupuncture needles and the following dimensions: 0.2×15 mm, 0.25×40 mm, 0.3×30 mm, 0.3×100 mm, 0.35×50 mm and 0.35×100 mm.

The material of the needle(s) for use as the first electrode is preferably metal. Preferred metals are stainless steels, i.e. unalloyed or alloyed steels with a low sulphur and phosphorus content. Other alloy elements are preferably chromium (preferably in an amount of 10.5-13 wt. % or higher), nickel (preferably in small amounts, such as maximum 10 wt. %), molybdenum, titanium and/or niobium. The preferred material is 18/10 chrome-nickel steel or medical stainless steel. Preferred steels are those that are resistant to water and weak organic and inorganic acids. In particular, stainless steels are preferred. Other preferred metals are silver, gold and platinum. The needles are optionally only silver-plated, or gold- or platinum-plated. Sintered materials made from silver/silver chloride, for example, are also preferred.

The first electrode comprises a multiplicity of needles, preferably 2-20, preferably 3-15, 3-12, 4-10, 5-9, 5-8, 6-9, 6-8 and in particular, 6 or 8. This allows a particularly good encircling of an area to be treated. In particular embodiments the first electrode can also comprise a larger number of needles, which is advantageous in particular if there is more than one area to be treated.

In the direct current output device according to the invention the tips of the multiplicity of needles of the first and optionally of the second electrode are preferably arranged along an essentially circular or elliptical circumference. The second electrode is preferably located outside of the region defined by the needles of the first electrode. These embodiments enable particularly advantageous treatments.

Alternatively, the needles are also arranged along a line which can be, for example, substantially straight, or also bent or curved.

In particular embodiments a first group of needles and one or more other group(s) of needles can also be provided (approx. two, three, four or five groups of needles as the first electrode), which allows a treatment of more than one region to be treated. In these embodiments it is preferable if the tips of the needles of the first group are arranged along a substantially circular or elliptical circumference and the tips of the needles of the other group(s) are (each) also arranged along a substantially circular or elliptical circumference. The second electrode is in this case preferably located outside of the regions defined by the needles. It is preferable for any electrically conductive connection of the needles to be formed along the respective (circular or elliptical) circumference of the individual groups of needles (series connection of the needles of the respective group) and/or the groups to each be connected in series by means of a single electrically conductive connection.

Alternatively, the tips of the needles of the first group are arranged along a line which is, for example, substantially straight or bent or curved, and the tips of the needles of the other group(s) can (each) also be arranged along a line which, for example, is substantially straight or bent or curved, wherein needles of the individual groups are preferably each connected in series and/or the groups are connected in series, in each case by a single electrically conductive connection.

Preferably, the first electrode (electrode for use in the area to be treated) is designed as a negative pole (cathode) and the second electrode as an anode (positive pole). This measure optimizes the treatment options when using the direct current output device according to the invention.

The second electrode is preferably designed as a flat electrode (variant A). Such an electrode can be used as a surface electrode and is preferably adapted for fitting on the surface of the body, for example by being configured as an adhesive electrode (as defined above). The electrode is preferably incorporated into an adhesive strip or otherwise connected to an adhesive strip. An adhesive effect can also be facilitated by electrode gel or electrode paste. Preferably, the material for the second electrode is selected from the group consisting of conductive rubber, conductive textile, conductive plastic, sponge (for example to be soaked with water or sodium chloride solution), sintered material (for example silver/silver chloride) and metal (for example, stainless steel, silver, gold and/or platinum).

Preferred sizes of a flat second electrode are 25 cm$^2$ to 200 cm$^2$, in particular 50 cm$^2$ to 100 cm$^2$.

Without being bound to a particular theory, it is assumed that a use of silver/silver chloride electrodes, especially in a chloride-containing medium such as the body, stabilizes the contact potential (junction potential) at the metal/electrolyte junction so that the current output can be even better controlled.

The second electrode optionally comprises a multiplicity of surface structures, for example, two, three, four or five.

In addition it is possible to design the second electrode as a needle (variant B), while for preferred configurations of this needle the statements relating to the needles of the first electrode apply.

Particularly preferred combinations of the first and second electrode are as follows: needle-shaped first electrode in combination with a needle-shaped second electrode and needle-shaped first electrode in combination with flat second electrode. The statement made above in relation to needle-shaped electrodes or flat electrodes applies. In particular, a needle-shaped second electrode optionally comprises, for example, a multiplicity of needles (for example, two, three, four or five or also as described for the first electrode) and/or a flat second electrode optionally comprises a multiplicity of surface structures (for example, two, three, four or five).

In accordance with an alternative embodiment, both electrodes are combined in a single structure (multi-pole needle). For example, this is advantageous in the treatment of a narrowly restricted area, or in patients for whom the application of electrodes is generally poorly tolerated. This according to the invention a needle can have the first electrode and the second electrode arranged one behind the other along its longitudinal extension, for example the cathode is closer to the end to be pierced than the anode, or the anode is closer to the end to be pierced than the cathode. The second electrode in this case is also either continuous or discontinuous. For example, the surface of the cathode and/or the anode can optionally be designed as one or more cylindrical jackets. In this case the surface of the first electrode is preferably designed as a multiplicity of cylindrical jackets and the surface of the second electrode as a cylindrical jacket or a multiplicity of cylindrical jackets.

The electrodes, the means for connecting the electrodes to the direct current source and/or the connections of the direct current source are preferably labelled according to their polarity, for example by color or shape, symbols, such as +and −, numbers or letters.

A physiologically acceptable current intensity, or one that is not harmful to the cells of the body tissue, is preferred. The maximum total current intensity of the direct current in the preferred variant A with a flat second electrode is preferably 2000 µA, preferably 1000, 700, 500, 400, 300, 250, 200, 150 or 100 µA. In the case of variant B with a needle as the second electrode, the maximum total current intensity of the direct current is preferably 1000, 750, 500, 250, 200, 150, 100, 50, 25 or 5 µA. The term "total current intensity" is understood as meaning the sum of the current intensities output by the individual needles of the first electrode.

The preferred minimum total current intensity of the direct current is 10, 20, 30, 40 or 50 µA (variant A) or 1, 1.5, 2 or 2.5 µA (variant B). Particularly preferable ranges for the current intensity are from 10-800 µA, 10-600 µA, 10-400 µA, 10-250 µA, 20-250 µA, 10-200 µA, 20-200 µA, 10-150 µA, 20-150 µA, 30-150 µA, 20-100 µA, 30-100 µA, 40-100 µA and 50-100 µA (variant A) or ranges from 1-100 µA, 1-50 µa, 1-25 µa, 1.5-20 µA, 2-15 µA, 2-10 µA and 2.5-5 µA (variant B). The direct current output device according to the invention preferably comprises a means for setting the total current intensity and in particular, a means for setting a minimum and/or maximum total current intensity, in all cases preferably by remote control.

The individual current intensities can be identical or different. The individual current intensities are preferably identical, in particular averaged over time, or the factor that is obtained by dividing the largest individual current by the smallest individual current, in particular averaged over time, is not greater than 2, 1.9, 1.8, 1.7, 1.6, 1.5, 1.4, 1.3, 1.25, 1.2, 1.18, 1.15, 1.12, 1.1, 1.08 or 1.05. In other cases, different individual current intensities can also be preferred; in such cases it is advantageous if the individual current intensities can be individually regulated.

Preferably, the variation of a single current intensity about its constant value is a maximum of 50% of the constant value, advantageously a maximum of 40%, 30%, 25%, 20%, 15%, 12%, 10%, 9%, 8%, 7%, 6%, 5%, 4%, 3%, 2% or 1%. This is preferably the case for all of the individual current intensities.

Preferred maximum and minimum individual current intensities are obtained from a preferred maximum or minimum total current and a preferred number of needles in the first electrode. Preferred maximum single current intensities are, for example, values of 6 µA, 8 µA, 10 µA, 12 µA, 14 µA, 16 µA, 18 µA, 20 µA, 30 µA, 40 µA, 50 µA, 60 µA, 70 µA, 80 µA, 90 µA, 100 µA, 110 µA, 120 µA, 130 µA, 140 µA, 150 µA, 160 µA, 170 µA, 180 µA, 190 µA, 200 µA, 250 µA, 300 µA, 350 µA, 400 µA, 450 µA, 500 µA, 550 µA, 600 µA, 650 µA or 700 µA (variant A) and 0.3 µA, 0.4 µA, 0.5 µA, 0.6 µA, 0.7 µA, 0.8 µA, 0.9 µA, 1 µA, 2 µA, 3 µA, 4 µA, 5 µA, 6 µA, 7 µA, 8 µA, 9 µA, 10 µA, 20 µA, 30 µA, 40 µA, 50 µA, 60 µA, 70 µA, 80 µA, 90 µA, 100 µA, 110 µA, 120 µA, 130 µA, 140 µA, 150 µA, 160 µA, 170 µA, 180 µA, 190 µA, 200 µA, 250 µA, 300 µA or 350 µA (variant B).

The current density, defined as the output current intensity in relation to the surface area contacted by a needle, preferably has a maximum value of 10 µA/mm$^2$, preferably a maximum of 7 µA/mm$^2$, a maximum of 5 µA/mm$^2$, a maximum of 3 µA/mm$^2$, a maximum of 2.5 µA/mm$^2$, a maximum of 2 µA/mm$^2$, a maximum of 1.5 µA/mm$^2$, a maximum of 1 µA/mm$^2$ or 0.5 µA/mm$^2$. The electrical voltage when using the direct current output device for treating the human body or body of an animal is preferably a maximum of 24 V, 20 V, 18 V, 16 V, 14 V, 13 V, 12 V, 11 V, 10 V, 9 V, 8 V, 6 V, 4.8 V, 4.5 V, 3.6 V, 3 V, 2.4 V, 1.5 V or 1.2 V. This ensures that harmful effects on the body are avoided. The direct current output device according to the invention preferably comprises a means (in particular remotely controllable) for adjusting a maximum voltage. It preferably also comprises a means (in particular remotely controllable) for adjusting a maximum charge.

The strength of the electric field is preferably in the range of 10-2500 mV/mm, in particular of 200-1500 mV/mm. The field density can be even higher in the environment of needle-shaped electrodes, which is a preferred treatment principle when using the direct current output device according to the invention. The strength and profile of the electric field in the environment of needle-shaped electrodes direct the effect when using the direct current output device according to the invention mainly into the area in which the electrode is applied, or into its immediate neighborhood. In the immediate environment of a needle-shaped electrode, the field intensity falls off exponentially in the orthogonal direction.

The direct current output device optionally also comprises a means for temporal control, with which multiple time intervals for outputting the direct current can be predefined. In the simplest case, this is an electronically switchable interruption of the electrically conductive connection between cathode, direct current source and anode. The means for temporal control is preferably linked to a means for setting a minimum time interval, wherein the latter preferably allows a definition of a minimum period of 1 s, 10 s, 1 min, 2 min, 5 min, 10 min, 20 min or 30 min. The means for temporal control can preferably be remote controlled. According to a preferred embodiment the means for temporal control is preferably linked to a (preferably remote controllable) means for defining a maximum time interval, wherein the latter preferably allows a definition of a maximum period of 2 h, 1 h, 50 min, 40 min, 30 min, 20 min, 10 min, 5 min or 2 min.

The direct current output device according to the invention preferably comprises a means (in particular remotely controllable) for ramping up and ramping down the current intensity. One such means allows an increase in the current intensity at the beginning of the treatment from zero up to the target value within a pre-definable time interval (with a preferred length of 1-60 seconds, particularly preferably 5-45 seconds and in particular 10-30 seconds), and at the end of the treatment a decrease from the target value down to zero within a pre-definable time interval (with a preferred length of 1-60 seconds, particularly preferably of 5-45 seconds, more preferably 10-30 seconds and in particular 15 seconds). A slow ramping up and ramping down of the current intensity is advantageous because otherwise—with a sudden switching of the current on or off—the individual being treated feels an unpleasant twitching or electrical shock sensation.

The direct current output device according to the invention preferably comprises a (preferably remotely controllable) means for changing over the polarity of the electrodes during a treatment. This is preferably linked to a means for temporal control, so that it is possible, for example, to change the polarity every second, every 10 seconds, every minute, every 2 minutes, or every 5 min or every 10 min.

The direct current output device can be optionally set into a test mode in which a constant voltage of approx. 1-8 V, 2-6 V or 3-5 V is supplied. This can be used to check whether the electrodes (for example in particular, all needles) are correctly electrically coupled or not, or whether a concealed cable breakage is present in any of the cables. The direct current output device preferably comprises a signal transducer (such as a tone generator) which indicates when a correct current flow is produced. From an absence of the signal, it can be concluded that the coupling chain has been interrupted.

A signal transducer can preferably also be used to indicate the beginning and/or the end of the treatment. A signal encoder can also preferably be used to indicate whether the current flow is interrupted during a treatment or the impedance of the patient is too high, in particular in combination with a shut-off means.

By using the test mode the individual electrodes (e.g. needles) can also be directly stimulated, and from the reaction of the patient (muscle spasms or pain in non-contractile tissue) the correct positioning of the electrode (in particular the needle) can be deduced, as further described below.

The kit according to the invention for producing a direct current output device (third aspect of the present invention) preferably additionally comprises an instruction manual for therapeutic or cosmetic treatment of a human or animal body, wherein the treatment is preferably as explained in more detail hereafter.

A preferred embodiment of the direct current output device comprises a direct current source, a first electrode and a second electrode for connecting to the direct current source, and one or more means for respectively keeping the current intensity constant during the individual output of the direct current through the needles of the first electrode, wherein the first electrode is designed as a multiplicity of electrically conductive needles which are not directly connected to each other and the second electrode is designed as a flat electrode. A maximum total current intensity of the direct current is preferably 2000 µA, more preferably 1000 µA, particularly preferably 700 µA and in particular, 500 µA. Of course, the lower current intensities given above can also be combined with this embodiment. A further preferred feature is a first electrode which comprises 2-20 needles. The individual current intensities in this case are preferably identical.

The direct current output device according to the invention is preferably used for the treatment of inflammations and/or pain, especially of the muscles, nerves, tendons or bones.

During the treatment an application of continuous current is preferable to an application of pulsed current. Alternatively possible are oscillating current intensity as described above or a non-periodically varying current intensity (which at each point in time has substantially the same value).

Preferably, the respective current intensity during the individual output of the direct current through the needles of the first electrode (or the value about which the respective current intensity oscillates) is kept constant, in particular also in the case where a resistance connected to one or more of the needles of the first electrode (in each case) changes.

The duration of a preferred treatment is between 1 min and 2 h, 5 min and 1 h, 10 min and 50 min, 20 min and 40 min and preferably 30 minutes. The treatment preferably comprises a total current output time of 60 min, 45 min, 30 min, or 20 min. The current output preferably takes place without interruption during the treatment. In accordance with an alternative embodiment however, the treatment can also comprise a plurality of predefined time intervals (for example, 2, 3, 4, 5, 6 or more preferably equally long time intervals) during which the direct current is applied, wherein a pause of 1 s to 5 min, 10 s to 3 min or 30 s to 1 minutes is preferably provided between the time intervals. Alternatively, the direct current can be switched on and off with a frequency of 0.01-1 Hz, preferably 0.02 to 0.2 Hz and in particular, 0.05 to 0.1 Hz. These time intervals or the on and off switching are controlled by the means for temporal control which may be provided (see above). At the beginning and at the end of the treatment the current intensity is preferably slowly ramped up or down respectively, for example over a period of 1-60 seconds, preferably 5-45 seconds and in particular 10-30 seconds and particularly preferably, 15 seconds.

The treatment preferably takes place within one day, in particular within a period of 4, 3 or 2 hours. Depending on the treatment approach, it is preferable to carry out treatment one or more times (in particular once, twice or three times per week or daily).

In the period prior to the current application the painful/inflamed area to be treated should preferably be circled and thus localized, preferably by deep pressure down to the bone from all sides. In the terminology of TCM a corresponding point which is painful under pressure is called "Ahshi". The area to be treated, following optional disinfection, is fitted with an electrode, preferably one or more needles (preferably by insertion), and in particular circumscribed with a multiplicity of needles (in particular in a circular or elliptical manner). Circumscription here preferably means that the needles are inserted along the border of this region. Other options exist, which involve inserting the needles a few millimeters outside the border or inside of the region. This insertion of the needle(s) should preferably be performed as deeply as possible (for example into the subcutis, into a muscle, into the ligaments or tendons, under the acromion, on the facets of the spine or on the periosteum), optionally with local anesthesia. Alternatively, the area to be treated can also be fitted with needles by arranging a multiplicity of needles along a substantially straight line, wherein the line intersects this area or is tangential to it or is also located outside of the area.

The second electrode is positioned on or in the body, and preferably outside of a region defined by one of the needles of the first electrode. In particular, the second electrode is positioned in a different region of the body than the first electrode. The second electrode (variant A: flat electrode) is preferably positioned above large groups of muscles or fat layers, so that it cannot stimulate individual nerves. A second electrode in accordance with variant B (needle-shaped electrode) is preferably applied intra-muscularly.

Preferably, prior to the actual treatment, it is verified by means of a brief application of a current that (an) inserted needle(s) is/are not in the vicinity of nerve roots, so that no pain reaction or motor response occurs during the treatment. Otherwise, the needle(s) would have to be slightly withdrawn or positioned at a different place.

Alternatively, in particular embodiments a twitching of a muscle can also be used deliberately to check the positioning of a needle. An electric current can be used to trigger a muscle twitch, for example by electrodes being held on inserted needles while current is output. The stronger this twitching, the better is the needle positioned. As already mentioned above, for example using the test mode described, it is possible to stimulate the individual electrodes (e.g. needles) directly, and from the response of the patient to deduce the correct positioning of the electrode (in particular, needle). Thus a needle inserted into an inflamed, painful muscle under direct test stimulation causes an increased muscle spasm compared to a needle inserted into a non-inflamed muscle. In the case of needles which penetrate non-contractile tissue, in direct test stimulation the patient feels increased pain (burning) around the needle in the inflamed tissue as compared to a non-inflamed area of tissue.

Optionally, a plurality of separately controllable current sources can also be used.

It is possible that, in addition to their anti-inflammatory and analgesic effect, the electric fields generated by the direct current output device according to the invention also have a reconstructive effect, for example due to a promotion of vascular growth, inter alia via the release of VEGF and an impact on endothelial cells. It is also possible that they give rise to a movement and rearrangement of cell membrane receptors, increase the division rate of certain cells, the migration of epithelial cells (especially towards the cathode) and accelerate the healing of wounds. It is also conceivable that the peripheral nerve regeneration after spinal cord trauma can be accelerated by growth towards the cathode, which would then preferably be applied cranially.

Without being bound to a particular theory, the effect of the application of the direct current output device according to the human or animal body can be attributed to the direct action of the administered electric current, or applied electric field, on the affected tissue or cells. One explanation is, for example, a change in the electrical excitability of cells, particularly nerve cells (de- or hyper-polarization), possibly via an effect on cation channels or via a temporary shift in the ion balance between intracellular and extracellular space. This could in particular involve an efflux of potassium ions and other cations into the extracellular space, which could explain a local anti-inflammatory and analgesic effect. A regeneration of aseptic wounds or degenerately modified tissue constituents or a migration from cells in the electrical field could also be (jointly) responsible for the observed effect. It is assumed without being bound to a particular theory that the electrical current administered or the electric field applied has a direct and local impact on fundamental inflammation processes, processes of pain formation and/or of tissue regeneration in the cells and in the tissue. This in turn influences basic electrophysiological/neurophysiological mechanisms.

The current intensity and voltage used here are many times smaller (several powers of ten) than those used in known electro-acupuncture devices. In particular, direct current and not alternating current is used.

In the case of known medical electro-stimulation devices the action principle is based on a high intensity of the voltage and/or current. For example, galvanic baths or cauterization are designed to cause heating of the tissue, or in the case of TENS (gate control theory) an above-threshold receptor stimulation for suppressing pain. In contrast to this, the direct current output device according to the invention operates with extremely small voltages, current intensities and electrical fields, which would generate in particular an inflammation-inhibiting, pain inhibitory and/or regenerative effect.

After insertion of a needle, between the negative pole of the needle and a large-area electrode stuck onto the skin, a potential difference of 100-300 mV, for example, is measured. By a quick manual rotation of the needle the potential difference can increase, which can be mainly attributed to the influence of the electrode contact potential, and subsequently drop back down logarithmically to the starting value. The insertion of needles and their manual stimulation are basic techniques of analgesic acupuncture.

The subject matter of the present invention is also the direct current output device according to the invention for use in the treatment of the following impairments or complaints: migraine, tension headache (e.g. migraine-like tension headache), neuralgias (e.g. post-herpetic neuralgia, occipital neuralgia, trigeminal neuralgia, neuralgia of the femoral nerve, in particular post-operatively), Herpes zoster (shingles) pain, neuropathic pain, post-herpetic pain, Bing-Horton syndrome, tinnitus, allergies, and inflammatory symptoms in allergy, cervical spine syndrome, thoracic spine syndrome, lumbar spine syndrome, chronic lower back pain, spinal canal stenosis, cervical brachialgia, sciatica, radiculitis, periarthritis humero scapularis, pain in osteoarthritis, osteoarthritis of the knee, arthritis (if not systemic), tendonitis (e.g. tennis elbow, golfer's elbow (epicondylitis lateralis or medialis), tenosynovitis, insertion tendinitis, achillodynia, heel spur, redness of the skin, inflammation of the skin, seborrhea, psoriasis, seborrheic or erythematous and/or psoriatic conditions, acne, hair loss (e.g. alopecia), mobility restrictions due to local irritation especially of the skin, such as local concretions and tensions.

The same applies to the use of the direct current output device according to the invention for treating the above indications, to the use of the direct current output device according to the invention for producing a therapeutic device for treating the above indications and to the method according to the invention for treating cases of inflammation and/or pain.

The direct current output device according to the invention preferably creates a long-term regenerative effect, preferably increasing from treatment to treatment, for example in chronic tendinitis or chronic neuropathic pain.

The following treatments are preferably excluded: Treatment of a hair follicle, treatment of open wounds and treatment of skin injuries.

In accordance with a further aspect the present invention relates to the use of the direct current output device according to the invention for the cosmetic treatment of the human or animal body.

The present invention according to a further aspect also relates to a method for producing a direct current output device comprising the following steps: providing a kit according to the invention (in accordance with the third aspect of the present invention), providing a direct current source, providing the multiplicity of needles to form the first electrode (wherein the tips of a multiplicity of needles are preferably arranged along a substantially circular or elliptical circumference or along a line which is substantially straight but also bent or curved), providing the flat electrode or the needle or directly electrically conductive connection of the multiplicity of needles to form the second electrode (wherein the tips of a multiplicity of needles are preferably arranged along a substantially circular or elliptical circumference or along a line which is substantially straight but also bent or curved, and the direct electrically conductive connection is preferably effected along the circumference), connecting the first electrode to the direct current source and connecting the second electrode to the direct current source.

A further aspect of the present invention is the direct current output device according to the invention for application in a method for therapeutic treatment of the human or animal body, or the use of the direct current output device according to the invention in a method for the therapeutic treatment of the human or animal body.

Finally, the present invention relates to an electric field that can be generated by the direct current output device according to the invention. The field maximum here is located around the needle body and a needle tip.

In addition the present invention relates to such an electric field for application in a method for therapeutic treatment of the human or animal body, in particular such an electrical field for treating cases of inflammation and/or pain, in particular of the muscles, nerves, tendons or bones or for treating any one of the above mentioned indications.

EXAMPLES

All the pain FIGURES contained in the following examples were determined with a visual analogue scale (VAS) and are given as a percentage of the output value.

Treatments in which a constant current intensity of the individual needles was not maintained are expressly marked as such; these are described for comparison purposes. All other treatments took place under constant current intensity of the individual needles, whether or not this is explicitly indicated.

Example 1

Pain in the Knee Joint 5 months of pain in the medial capsule area of the right knee joint. Pain area approximately 2 cm long and 0.5 cm wide. Place 3 needles, 0.3×30 mm, current intensity per needle 45 µA, ±10%, total current intensity 135 µA. Duration of stimulation 30 min. Immediately after the end of treatment approx. 40% improvement, after approx. 2 h pain-free. Duration of effect 4 days. Then slight relapse. Re-treatment in the same manner. After one day complete and sustained freedom from symptoms.

Example 2

Post-Shingles Neuralgia

Patient, male, 82 years old. After an episode of herpes zoster (shingles) very severe neuropathic pain and tingling paraesthesia on the left side of the thorax for the last 4 years, extending from the thoracic vertebrae to the nipple. Insertion of 0.3×30 mm needles subcutaneously around the pain area, a total of 16 needles. Stimulation with 20 µA per needle—total current intensity 320 µA, no improvement. Re-treatment with 60 µA per needle—total current intensity 960 µA. Directly after the therapy, pain alleviated. Subsequently 50% pain reduction over more than one week, third treatment again with 60 µA per needle, then further improvement to a total of 80% pain relief within 2 h. After further treatment 90% improvement.

Example 3

Heel Pain with Insertion Tendinitis of the Achilles Tendon

Female patient, 34 years, heel pain for 6 months with bone marrow edema and in addition, pain with slight inflammatory changes in the attachment region of the Achilles tendon on the calcaneus. Placement of 3 needles 0.35×50 mm in the area of the heel and 5 needles 0.15×20 mm in the area of the Achilles tendon. Stimulation with a total of 240 µA without holding the current intensity of the individual needles constant. The next day, improvement of the heel pain, but no change in the Achilles tendon. Re-treatment, this time holding each needle constant at 30 µA, total stimulation with 240 µA. After 3 h, improvement in heel pain and also in Achilles tendon pain by 80%.

Example 4

Biceps Tendon Tear, Condition After Surgery

Handball player, 24 years old. Over a period of 6 months following shoulder surgery, continued pain in the bicep tendon of the right upper arm. Jobe's test positive. Unfit for playing or training. First treatment with a total of 120 µA on 5 needles 0.25×40 mm, without holding current intensity of the individual needles constant. No improvement. Second treatment with 240 µA on 8 needles 0.35×50 mm, without holding current intensity of individual needles constant, no improvement. Third treatment with 50 µA per needle, with constant current intensity of each individual needle, a total of 8 needles 0.35×50 mm, total current 450 µA. After 3 h subjective improvement, next day 50% improvement. Repetition of the last treatment 3 times in total, thereafter sport-specific training possible. Total improvement of 90%.

Example 5

Migraine

For many years, approx. 6 migraine days/month. Nausea, also occasional vomiting. Pain radiation behind head to right temple. Pulsating pain. First treatment took place during a headache phase. Placement of 3 needles 0.25×40 on rear of head and 4 needles 0.2×20 in the painful area of the forehead and temple, without holding the current intensity of the individual needles constant. After the treatment pain increased, in particular at the back of the head. Second treatment with constant current in each individual needle at 20 µA. During the treatment, abatement of nausea. Two hours after the treatment, cessation of headache. In the following 8 weeks, only two migraine days instead of the expected 12 migraine days. Re-treatment in identical manner. Further improvement to one headache day/month, but without nausea and vomiting.

What is claimed is:

1. A therapeutic direct current application device, comprising:
   a direct current source;
   a first electrode including a first electrode first end configured to be connected to a first pole of the direct current source, and a first electrode second end configured to be applied to a first body region, wherein said first electrode second end comprises a first plurality of electrically conductive needles;
   a second electrode including a second electrode first end configured to be connected to a second pole of the direct current source, and a second electrode second end configured to be applied to a second body region, wherein said second electrode second end comprises at least one of a flat electrode, a needle, and a second plurality of electrically conductive needles; and
   a plurality of means for individually maintaining a constant direct current of a predetermined value through each of the first plurality of electrically conductive needles of the first electrode, when the first electrode second end is applied to the first body region and the second electrode second end is applied to the second body region.

2. The direct current application device of claim 1, wherein each of the plurality of electrically conductive needles of the first electrode is electrically separate from each other of the plurality of electrically conductive needles.

3. The direct current application device of claim 1, wherein the second electrode comprises a flat electrode.

4. The direct current application device of claim 1, wherein the means for maintaining the constant direct current is automated.

5. The direct current application device of claim 1, wherein the means for maintaining a constant direct current comprises at least one of a regulator and a series resistor.

6. The direct current application device of claim 1, wherein the direct current source comprises a current source connector for connection to a current source for direct current, wherein the current source connector includes a first end of a first connector configured to be connected to a first pole of the current source for direct current and a first end of a second connector configured to be connected to a second pole of the current source for direct current;
   wherein the first electrode first end is configured to be connected to the second end of the first connector to connect the first electrode first end to the first pole; and
   wherein the second electrode first end is configured to be connected to the second end of the second connector to connect the second electrode first end to the second pole.

7. The direct current application device of claim 1, wherein each of the plurality of individual electrically conductive needles is configured for independent application to a location on the first body region.

8. The direct current application device of claim 1, wherein the direct current source is configured to simultaneously stimulate each of the first plurality of electrically conductive needles of the first electrode via the means for maintaining a separate constant direct current of the predetermined value through each of the first plurality of electrically conductive needles of the first electrode.

9. A direct current application device, comprising:
   a direct current source;
   a first electrode including a first electrode first end configured to be connected to a first pole of the direct current source, and a first electrode second end configured to be applied to a first body region, wherein said first electrode second end comprises a first plurality of electrically conductive needles;
   a second electrode including a second electrode first end configured to be connected to a second pole of the direct current source, and a second electrode second end configured to be applied to a second body region, wherein said second electrode second end comprises one of a flat electrode, a needle, and a second plurality of electrically conductive needles; and a plurality of at least one of a regulator and a series resistor configured to individually maintain a constant direct current of a predetermined value through each of the first plurality of electrically conductive needles of the first electrode, when the first electrode second end is applied to the first body region and the second electrode second end is applied to the second body region.

10. The direct current application device of claim 9, wherein the one of the regulator and the series resistor is further configured to permit individual adjustment of the constant current provided through each of the first plurality of electrically conductive needles of the first electrode.

11. The direct current application device of claim 9, wherein the first electrode comprises a cathode.

12. The direct current application device of claim 9, wherein tips of the first plurality of electrically conductive needles of the first electrode are arranged along one of a substantially circular circumference and an elliptical circumference, and wherein two or more needles of the first plurality of conductive needles that are along the one of the substantially circular circumference and the elliptical circumference are electrically connected.

13. The direct current application device of claim 12, wherein the at least one of the regulator and the series resistor comprises a regulator, the regulator being configured to measure an actual direct current value, define a deviation of the actual direct current value from the direct current of the predetermined value, and adjust a voltage in proportion to the deviation to adjust the actual direct current value to maintain the direct current of the predetermined value.

14. The direct current application device of claim 12, wherein the at least one of the regulator and the series resistor comprises the series resistor, the series resistor comprising one or both of fixed resistors and variable resistors of a value selected to minimize an effect of skin resistance in the therapeutic treatment, to maintain the constant direct current of the predetermined value through each of the first plurality of electrically conductive needles of the first electrode.

15. The direct current application device of claim 14, wherein the series resistor has a resistance of 10 kΩ to 100 kΩ.

16. A method for therapeutic treatment using a direct current, comprising:
  connecting, to a first pole of a direct current source, a first electrode including a first electrode first end, and a first electrode second end configured to be applied to a first body region, wherein said first electrode second end comprises a first plurality of electrically conductive needles;
  connecting, to a second pole of the direct current source, a second electrode including a second electrode first end and a second electrode second end configured to be applied to a second body region, wherein said second electrode second end comprises one of a flat electrode, a needle, and a second plurality of electrically conductive needles; and
  applying the second electrode second end to the second body region;
  applying the first electrode second end to the first body region to apply the constant direct current of the predetermined value to the first body region to provide the therapeutic treatment to the first body region, wherein the first electrode second end comprises one or more of the plurality of electrically conductive needles of the first electrode; and
  individually maintaining, by at least one of a regulator and a series resistor for each of the first plurality of electrically conductive needles, a constant direct current of a predetermined value through each of the first plurality of electrically conductive needles of the first electrode, while the first electrode second end is applied to the first body region and the second electrode second end is applied to the second body region.

17. The method of claim 16, wherein the therapeutic treatment comprises cosmetic treatment.

18. The method of claim 16, wherein the first body region and second body region correspond to one of a human body and an animal body.

19. The method of claim 16, wherein providing the therapeutic treatment comprises one or both of providing an inflammation treatment and a pain treatment.

20. The method of claim 16, wherein the first body region corresponds to one of a muscle, a nerve, a tendon, and a bone.

21. The method of claim 16, wherein the second electrode comprises a flat electrode, and wherein the applying the constant direct current comprises applying a maximum direct current of 2000 μA.

22. The method of claim 16, wherein the second electrode comprises a needle, and wherein the applying the constant direct current comprises applying a maximum direct current of 100 μA.

* * * * *